United States Patent [19]

Koenig et al.

[11] Patent Number: 4,948,909

[45] Date of Patent: Aug. 14, 1990

[54] PROCESS FOR THE PREPARATION OF IMINODIACETONITRILE AND IMINODIACETIC ACID

[75] Inventors: Karl E. Koenig, Ballwin; Gary A. Lanser, Pacific; Paul A. Morrison, Arnold; Robert B. Weisenfeld, Manchester, all of Mo.

[73] Assignee: Monsanto Company, St. Louis, Mo.

[21] Appl. No.: 394,039

[22] Filed: Aug. 14, 1989

[51] Int. Cl.$^5$ ............................................. C07C 253/30
[52] U.S. Cl. ...................................... 558/346; 562/571
[58] Field of Search ........................... 558/346; 562/571

[56] References Cited

U.S. PATENT DOCUMENTS

| | | | |
|---|---|---|---|
| H4 | 12/1985 | Cullen | 558/346 |
| 3,886,198 | 5/1975 | Philbrook et al. | 558/346 X |
| 3,988,360 | 10/1976 | Gaudette et al. | 558/346 |
| 4,307,037 | 12/1981 | Suchsland et al. | 558/346 |
| 4,661,614 | 4/1987 | Most et al. | 558/346 |

*Primary Examiner*—Joseph Paul Brust
*Attorney, Agent, or Firm*—Frank D. Shearin

[57] ABSTRACT

An improved process is provided for producing iminodiacetonitrile by contacting ammonia, formaldehyde and hydrogen cyanide, or hexamethylenetetramine, formaldehyde and hydrogen cyanide in a reaction medium, the improvement which comprises the further steps of thereafter adjusting the pH of the reaction medium to a pH between about 5.5 and about pH 10 and heating the reaction medium to an elevated temperature for a sufficient time to convert by-products in the reaction medium to iminodiacetonitrile.

11 Claims, No Drawings

PROCESS FOR THE PREPARATION OF IMINODIACETONITRILE AND IMINODIACETIC ACID

BACKGROUND OF THE INVENTION

The present invention is directed to a process for the preparation of iminodiacetonitrile (IDAN) and iminodiacetic acid (IDA) and derivatives thereof.

It is well known that IDAN is a valuable intermediate to prepare compounds such as IDA. It is also well known that IDA is a valuable intermediate for the preparation of other compounds. In fact, IDA is produced in commercial quantities in the United States for use as an intermediate in the preparation of numerous other compounds. Numerous methods are known in the art to prepare both IDAN and IDA.

For example, U.S. Pat. No. 3,886,198 to Philbrook, et al., discloses a process for preparing IDAN by preparing an aqueous mixture of hexamethylenetetramine, hydrogen cyanide and a strong acid such as sulfuric acid, hydrochloric acid and nitric acid, the aqueous mixture having a pH of 3 to 5 and a mole ratio of hexamethylenetetramine to hydrogen cyanide of 1 to 5-7. The aqueous mixture is passed through a tubular reactor reaction zone at a temperature between 50° C. and 120° C.

U.S. Pat. No. 3,988,360 to Gaudette, et al., discloses a continuous process for preparing IDAN by continuously preparing an aqueous reaction mixture of hexamethylenetetramine, formaldehyde and hydrogen cyanide having a mole ratio of hexamethylenetetramine to formaldehyde to hydrogen cyanide of 1 to 1-2.2 to 6.9-8.6 in a continuous reaction zone by continuously feeding an aqueous hexamethylenetetramine solution having a temperature of 0°-80° C., an aqueous formaldehyde solution having a temperature of 0°-80° C., and hydrogen cyanide having a temperature of 0°-25° C. into a continuous reaction zone at a temperature between 50° and 250° C. The pH of the resulting aqueous reaction mixture is between 5 and 10. The resulting IDAN can be recovered, or it can be hydrolyzed to form an alkali metal salt of IDA, which can be recovered or converted to IDA by acidification.

U.S. Pat. No. 4,307,037 to Suchsland, et al., discloses a process for the production of IDAN by reaction of hexamethylenetetramine with hydrogen cyanide in acidic aqueous mediums. In the process, the pH during the reaction is between 5.5 and 7.5 at the beginning, and is progressively lowered during the reaction by about 0.5 to 3.5 units by the addition of acid.

United States Statutory Invention Registration H4 to Cullen discloses a process for preparing IDAN by the reaction of 1 mole equivalent of hexamethylenetetramine, 2 mole equivalents of formaldehyde, and 8 mole equivalents of hydrogen cyanide at a temperature between about 20° and 90° C. and at a pH between 5.5 and 6.5.

Although satisfactory results can be achieved by these prior art processes, all of them suffer from one or more disadvantages. All of the prior art processes produce unwanted by-products such as glycolonitrile, aminoacetonitrile, ammonium salts, and the like. Now, there is provided an improvement to the prior art processes which converts most of the by-products to the desired IDAN, IDA, and derivatives thereof, and increases the overall yields. Because the quantity of the by-products is reduced, disposal of these by-products is significantly simplified.

SUMMARY OF THE INVENTION

These and other advantages are achieved in a process for producing iminodiacetonitrile by contacting ammonia, formaldehyde and hydrogen cyanide or hexamethylenetetramine, formaldehyde and hydrogen cyanide in a reaction medium, the improvement which comprises the further steps of thereafter adjusting the pH of the reaction medium to a pH between about pH 5.5 and about pH 10.0 and heating the reaction medium to an elevated temperature for a sufficient time to convert by-products in the reaction medium to iminodiacetonitrile.

DESCRIPTION OF THE PREFERRED EMBODIMENTS

As noted above, numerous methods are known to those skilled in the art on the preparation of IDAN and IDA. Generally, this involves the reaction at a pH between about 3-7 of ammonia, formaldehyde, and hydrogen cyanide at temperatures up to about 120° C. On the other hand, an aqueous reaction mixture of hexamethylenetetramine, formaldehyde and hydrogen cyanide can be reacted at temperatures up to 250° C. The actual process used to prepare the IDAN and IDA is not critical in the improved process of the present invention.

However, we have found that the process of the present invention is particularly applicable to a process for producing IDAN, or its hydrolyzable products, and IDA by reacting 2 mole equivalents of formaldehyde with 1 mole equivalent of hexamethylenetetramine and 8 mole equivalents of hydrogen cyanide in the presence of a strong mineral acid, such as hydrochloric acid, sulfuric acid, nitric acid and the like, to produce 4 mole equivalents of IDAN. This reaction is typically run at modest temperatures, say between about 20° C. and 60° C. at a pH between about 5 and about 6. This process reduces the amount of unwanted by-products, such as glycolonitrile, aminoacetonitrile and ammonium salts. Hydrochloric acid or sulfuric acid are preferred as the strong mineral acid, which produces an ammonium salt as a by-product.

Regardless of the method by which the IDAN and IDA is produced from hexamethylenetetramine, or its precursors, ammonia and formaldehyde, by reacting the hexamethylenetetramine with formaldehyde and hydrogen cyanide, the improvement according to the present process converts unwanted by-products such as glycolonitrile, aminoacetonitrile and the ammonium salts to the desired IDAN, salts of IDA, and derivatives thereof. It is not important in the process of the present invention whether the IDAN or its derivatives is produced in a continuous or in a batch process. The improved process comprises the additional steps of adjusting the pH of the reaction medium to a pH between about pH 5.5 and about pH 10.0, and heating the reaction medium to an elevated temperature for a sufficient time to convert the by-products in the reaction medium to IDAN or its derivatives.

The IDAN goes through a series of derivatives to end at the disalts of IDA, depending on the temperature and the pH of the reaction medium. These derivatives can be prepared through routine experimentation in view of the present disclosure by those skilled in the art.

It has been found that the presence of glycolonitrile enhances the conversion of the by-products to the desired IDAN, or its hydrolyzable products. Although ammonium salts and aminoacetonitrile can be converted to the desired compounds in the absence of glycolonitrile, longer reaction times are required to avoid poor yields. It is preferred to have a molar excess of glycolonitrile over the amount of aminoacetonitrile and ammonium salts in the reaction medium to obtain high yields of the desired compounds in a reasonable time.

In the improved process of the present invention, the pH of the reaction medium is adjusted to between about pH 5.5 and about pH 10.0. At pH below about 5.5, the conversion of the by-products to the desired IDAN and its derivatives is significantly slower, and at a pH above about pH 10.0, the yields are poorer due to the formation of undesirable by-products, although some IDAN and its derivatives are formed. It is preferred to adjust the pH of the reaction medium to between about pH 6 and about pH 8.

As will occur to those skilled in the art, any number of means can be used to adjust the pH of the reaction medium. Suitable materials to adjust the pH include the alkali metal hydroxides, such as sodium hydroxide, potassium hydroxide, lithium hydroxide and the like, or the addition of an alkali metal carbonate, such as sodium carbonate, potassium carbonate and the like. Alkaline earth hydroxides, such as calcium hydroxide or alkaline earth carbonates, such as calcium carbonate can also be used to adjust the pH of the reaction medium. As will occur to those skilled in the art, ammonium hydroxide and ammonium carbonate should be avoided. The alkali metal hydroxides are preferred. Sodium hydroxide is especially preferred because of its ready availability and inexpensive price.

In the process of the present invention, the temperatures can vary within wide ranges. At temperatures much over 100° C., side reaction that form color bodies occur. Preferably, the reaction medium containing a molar excess of glycolonitrile to aminoacetonitrile and ammonium salt is heated to a temperature between about 50° C. and about 80° C. At temperatures below about 50° C., the conversion of the by-products to the desired IDAN or its derivatives is quite slow. It is especially preferred to heat the reaction medium to temperatures between about 60° C. and about 80° C.

At the temperatures of 50° to 100° C. and at a pH between about 5.5 and about 10.0, the reaction is completed within about 5 hours. At temperatures between about 60° C. and 80° C. at the preferred pH between about pH 6 and pH 8, the reaction according to the process of the present invention is complete in less time, frequently within two hours.

In the process of the present invention, it is preferred to separate at least some of the IDAN from the reaction medium before the pH of the reaction medium is adjusted and the reaction medium is heated. The IDAN can be separated from the reaction medium by any number of means known to those skilled in the art, such as by filtration, centrifugation, and the like. After at least some of the IDAN has been separated from the reaction medium and pH of the reaction medium has been adjusted and the reaction medium heated to convert the by-products in the reaction medium to IDAN or its derivatives, the separated IDAN can then be recombined with the reaction medium and hydrolyzed with an alkali metal hydroxide to form the disalt of IDA. The disalt can be used as a intermediate, or it can be acidified to form IDA. The hydrolysis of the IDAN occurs at a higher pH under conditions known to those skilled in the art. The formation of IDA from its disalt requires only the addition of acid, such as a strong mineral acid, under conditions known to those skilled in the art.

The invention is further illustrated by, but not limited to, the following Examples.

EXAMPLE 1

This example illustrates one embodiment of the present invention wherein IDAN is not separated from the reaction medium before the by-products are converted to the desired compounds.

Into a 150 ml Ace jacketed flask, equipped with a stirrer, a thermometer and a pH probe, was added hexamethylenetetramine (34.15 g), 36% hydrochloric acid (6.25 g), 50% formalin (30.4 g), water (34.45 g) and hydrogen cyanide (53.8 g). The pH of the reaction was about pH 5.5. The mixture was heated from room temperature to 75° C. for two hours. Then, the pH was adjusted to pH 7 with 0.1 M sodium hydroxide. After an additional two hours of heating at 75° C. the contents were analyzed by HPLC. The yield composite of IDAN was 96%.

EXAMPLE 2

This example illustrates another embodiment wherein the IDAN is separated from the reaction medium before the by-products are converted to the desired compounds.

The procedure of Example 1 was repeated, except that after the first heating step for two hours, the reaction medium was allowed to cool to room temperature and the reaction mixture was filtered. The isolated yield of IDAN was determined to be 79% for this step. The filtrate was transferred to a 250 ml round bottomed flask, the pH was adJusted to pH 7, and the filtrate was heated to 75° C. for two hours. The resulting matrix was recombined with the IDAN from the first filtration for a composite yield of 97%.

Although the invention has been described in terms of specified embodiments which are set forth in considerable detail, it should be understood that this is by way of illustration only since alternative embodiments and operating techniques will become apparent to those skilled in the art in view of the disclosure. For example, although the improved process of the present invention has been described in terms of a batch operation, it is clear that it could be conducted in a continuous manner. Accordingly, modifications can be made without departing from the spirit of the described invention.

What is claimed is:

1. A process for producing iminodiacetonitrile which comprises:
    A. contacting ammonia, formaldehyde and hydrogen cyanide, or hexamethylenetetramine, formaldehyde and hydrogen cyanide, in a reaction medium to form iminodiacetonitrile; and;
    B. without recycle thereafter adjusting the pH of the reaction medium to a pH between about 5.5 and about 10.0 and heating the reaction medium to an elevated temperature for a sufficient time to convert by-products in the reaction medium to iminodiacetonitrile.

2. The process of claim 1 wherein the reaction medium in Step B is heated to a temperature between about 50° C. and about 100° C.

3. The process of claim 2 wherein the reaction medium is heated to a temperature between about 60 °C. and about 80° C.

4. The process of any of claims 1, 2 or 3 wherein the pH of the reaction medium of Step B is adjusted to between about pH 6 to about pH 8.

5. The process of claim 1 wherein the pH of the reaction medium in Step B is adjusted by adding an alkali metal hydroxide, an alkali metal carbonate, and alkaline earth hydroxide or an alkaline earth carbonate.

6. The process of claim 5 wherein the pH is adjusted by adding an alkali metal hydroxide.

7. The process of claim 6 wherein the alkali metal hydroxide is sodium hydroxide.

8. The process of claim 1 comprising the additional step of hydrolyzing the iminodiacetonitrile.

9. A process for producing iminodiacetonitrile which comprises:
   A. contacting hexamethylenetetramine, formaldehyde and hydrogen cyanide in a reaction medium;
   B. separating at least some of the iminodiacetonitrile from the reaction medium;
   C. without recycle, adjusting the pH of the reaction medium to between the pH 6 about pH 8; and
   D. heating the reaction medium to a temperature between about 50° C. and about 100° C. for a sufficient time to convert by-products in the reaction medium to iminodiacetonitrile.

10. The process of claim 9 wherein the pH of the reaction medium is adjusted by adding an alkali metal hydroxide to the reaction medium.

11. The process of claim 9 wherein the reaction medium in Step D is heated to temperatures between about 60° C. and about 80° C.

* * * * *